(12) United States Patent
Schabbach et al.

(10) Patent No.: US 10,105,093 B2
(45) Date of Patent: Oct. 23, 2018

(54) CALCULATING A MEDICAMENT DOSE

(75) Inventors: Michael Schabbach, Frankfurt am Main (DE); Jörg Heisiep, Frankfurt am Main (DE); Stephan Müller-Pathle, Frankfurt am Main (DE); Ross MacArthur, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 690 days.

(21) Appl. No.: 14/004,768

(22) PCT Filed: Mar. 15, 2012

(86) PCT No.: PCT/EP2012/054561
§ 371 (c)(1),
(2), (4) Date: Sep. 12, 2013

(87) PCT Pub. No.: WO2012/126800
PCT Pub. Date: Sep. 27, 2012

(65) Prior Publication Data
US 2014/0005501 A1   Jan. 2, 2014

(30) Foreign Application Priority Data

Mar. 18, 2011 (EP) .................... 11158875

(51) Int. Cl.
*A61B 5/00* (2006.01)
*A61B 5/145* (2006.01)
(Continued)

(52) U.S. Cl.
CPC ........ *A61B 5/4839* (2013.01); *A61B 5/14532* (2013.01); *A61B 5/222* (2013.01); *A61B 5/02438* (2013.01); *A61B 2562/0219* (2013.01)

(58) Field of Classification Search
CPC . A61B 5/4836; A61B 5/4839; A61B 5/14532; A61B 5/221; A61B 5/222; A61B 5/02438
(Continued)

(56) References Cited

U.S. PATENT DOCUMENTS 9,603,562 B2    3/2017 Aceti et al.
2003/0055406 A1*  3/2003 Lebel ................. A61N 1/37211
                                                              604/891.1
(Continued)

FOREIGN PATENT DOCUMENTS

EP    1281351 A2    2/2003
EP    1498067 A1    1/2005
(Continued)

OTHER PUBLICATIONS

English Translation of Abstract of Japanese Patent Application No. 2004-000555 dated Oct. 26, 2017.
(Continued)

*Primary Examiner* — John R Downey
(74) *Attorney, Agent, or Firm* — McCarter & English, LLP

(57) ABSTRACT

A device comprising:
  means for obtaining a parameter of a sample of body fluid from a user;
  means for using information provided by one or more sensors to calculate a measure of physical activity of the user;
  means for calculating a medicament dose using at least in part the measured parameter and the measure of physical activity of the user; and
  means for indicating the calculated medicament dose to the user.

13 Claims, 13 Drawing Sheets

(51) Int. Cl.
    *A61B 5/22*     (2006.01)
    *A61B 5/024*     (2006.01)

(58) Field of Classification Search
    USPC .................................................. 600/300, 301
    See application file for complete search history.

(56) References Cited

U.S. PATENT DOCUMENTS

| | | |
|---|---|---|
| 2003/0104982 A1 | 6/2003 | Wittmann et al. |
| 2003/0208110 A1 | 11/2003 | Mault et al. |
| 2003/0208113 A1 | 11/2003 | Mault et al. |
| 2005/0234309 A1* | 10/2005 | Klapper ............... A61B 5/1101 600/300 |
| 2009/0209938 A1* | 8/2009 | Aalto-Setala ...... A61B 5/02438 604/503 |
| 2010/0198142 A1* | 8/2010 | Sloan ................ A61B 5/14532 604/66 |

FOREIGN PATENT DOCUMENTS

| | | |
|---|---|---|
| JP | 2003533318 A | 11/2003 |
| JP | 2004000555 A | 1/2004 |
| JP | 2004024699 A | 1/2004 |
| JP | 2005525149 A | 8/2005 |
| JP | 2005267364 | 9/2005 |
| WO | 2009008612 A2 | 1/2009 |
| WO | 2009105709 A1 | 8/2009 |
| WO | 2010089307 A1 | 8/2010 |

OTHER PUBLICATIONS

English Translation of Abstract of Japanese Patent Application No. 2004-024699 dated Oct. 26, 2017.
English Translation of Abstract of Japanese Patent Application No. 2005-267364 dated Oct. 26, 2017.

* cited by examiner

CALCULATING A MEDICAMENT DOSE

CROSS REFERENCE TO RELATED APPLICATIONS

The present application is a U.S. National Phase Application pursuant to 35 U.S.C. § 371 of International Application No. PCT/EP2012/054561 filed Mar. 15, 2012, which claims priority to European Patent Application No. 11158875.2 filed Mar. 18, 2011. The entire disclosure contents of these applications are herewith incorporated by reference into the present application.

FIELD OF INVENTION

The present invention relates to calculating a medicament dose. In particular, the invention relates to a device for calculating a medicament dose and to a method of operating a device including calculating a medicament dose.

BACKGROUND

People with diabetes are either deficient in insulin or are unable to make sufficient insulin to overcome underlying insulin resistance or to normalize their glucose metabolism. In order to achieve a better glycemic control or even to regain almost full glycemic control, often basal insulin or insulin glargine treatments are used which are based upon a set of rules for periodic blood glucose measurements in order to obtain information on the progress of the treatment. With regard to this it has to be considered that the blood glucose levels fluctuate throughout the day. A "perfect glucose level" may mean that glucose levels are always in a range of 70 to 130 mg/dl or 3.9 to 7.2 mmol/l and/or undistinguishable from a person without diabetes.

In order to achieve this or to get as close as possible to such a "perfect glycemic control" blood glucose values are monitored once or several times during the day as relying on their own perception of symptoms of hyperglycemia or hypoglycemia is usually unsatisfactory as mild to moderate hyperglycemia causes no obvious symptoms in nearly all patients. If the blood glucose value is too high, e.g. over 130 mg/dl, insulin or insulin analogues can be administered.

For the insulin therapy, long-acting basal insulin or insulin glargines, which are long-acting basal insulin analogues, are used. These insulin or insulin analogues are usually given once or twice daily to help control the blood sugar level of patients with diabetes. The advantage of long-acting basal insulin or insulin glargine is that they have a duration of action of up to 24 hours or even more, and have a less peaked profile than NPH insulin.

For good or perfect glycemic control the dose of basal insulin or insulin glargine has to be adjusted for each individual in accordance with a blood glucose level to be achieved. Usually, the dose of insulin or insulin glargine is increased from an initial dose to a final dose over a certain time period until a specific blood glucose value, typically the fasting blood glucose (FBG) value, has reached the target range. In practice, such titration can be done by the health care professionals (HCPs). However, the patient may be empowered and trained by the health care professionals to do their own titration. Such a self-titration can be supported by an intervention from a third party support or services or some intermediate combination.

In the every day use, basal insulin or insulin glargine are typically under-dosed. Thus, there remains a gap between the initial dosing and an optimal dosing for achieving perfect or almost perfect glycemic control. This has a number of negative effects which better titration could help to eliminate. For example, if patients are not titrated, their blood sugar does not come down and as a result they do not feel better in the short term. Moreover, in the long term their HbA1c value (glycated haemoglobin) remains high and their long-term health suffers. Thus, the patients may feel that their treatment is not working and they may lose interest in the therapy or discontinue treatment.

Due to the almost peakless profile, basal insulin and insulin glargine are simple to titrate. Meanwhile, there is an array of approaches that physicians use for titration. Generally, these approaches suggest a specific dose adjustment within a specific time period until the target fasting blood glucose level (FBG) is achieved. Each of these algorithms comes with specific rules, e.g. that the dose should not be increased if the blood glucose value (BG value) was below 70 mg/dl (low blood sugar) in the last week. Furthermore, health care professionals may set a different FBG target to suit the patient.

EP 1 281 351 A2 describes a diabetes management system which enables glycemic control for a subject. The described system includes an insulin delivery unit, a glucose sensor and a control unit. The control unit includes a processor unit that receives glucose value readings from the glucose sensor, executes an algorithm that predicts a glucose value at a predetermined time in the future, compares the predicted glucose value with the predetermined glucose value range, and determines a corrective amount of insulin to be administered when the predicted glucose value lies outside of the predetermined glucose value range. The glucose unit also includes a communication unit that transmits the corrective amount to the delivery unit.

WO2010/089307 discloses a blood glucose meter that calculates a dose of e.g. insulin to be delivered to a user. An algorithm is used to calculate the dose based on a measured blood glucose level, user inputs and recent blood glucose levels. The calculated dose is displayed to the user.

SUMMARY

A first aspect of the invention provides a device comprising:
  means for obtaining a parameter of a sample of body fluid from a user;
  means for using information provided by one or more sensors to calculate a measure of physical activity of the user;
  means for calculating a medicament dose using at least in part the measured parameter and the measure of physical activity of the user; and
  means for indicating the calculated medicament dose to the user.

The parameter may be a concentration of glucose. The parameter may be another analyte parameter. The parameter may be a concentration, although other parameters are not precluded.

The means for calculating the medicament dose may be configured to use also a measure of physical activity intensity to calculate the medicament dose.

The means for calculating the medicament dose may be configured to use also a time elapsed between an instance of physical activity and a current time to calculate the medicament dose.

The means for calculating the medicament dose may be configured to use also a duration of physical activity to calculate the medicament dose. Here, the means for calculating the medicament dose may be configured to integrate physical activity intensity with respect to time and to use the result of the integration to calculate the medicament dose.

The one or more sensors may include a pedometer and the measure of physical activity may be a number of steps taken by the user within a predetermined period. Here, the pedometer may be integrated with the device.

The one or more sensors may include an accelerometer integrated with the device.

The device may include a communications receiver configured to receive information from external one or more sensors. Here, the device may be configured to verify that information received using the communications receiver relates to a user registered with the device and to disregard information other than verified information when calculating the medicament dose. In either case, the device may be configured to receive information relating to heart rate and/or blood pressure of a user and to calculate the measure of physical activity by processing the heart rate and/or blood pressure information. Alternatively or in addition, the device may be configured to receive information relating to a number of steps taken by a user from an external pedometer and to calculate the measure of physical activity by processing the steps information. Further alternatively or in addition, the device may be configured to receive information relating to work done by the user or power exerted by the user from an external ergometer and to calculate the measure of physical activity by processing the work done or power information.

The means for obtaining a parameter may comprise blood glucose measurement means.

A second aspect of the invention provides a device comprising:
  a receiver for obtaining a parameter of a sample of body fluid from a user;
  a calculator for using information provided by one or more sensors to calculate a measure of physical activity of the user and for calculating a medicament dose using at least in part the measured parameter and the measure of physical activity of the user; and
  an indicator for indicating the calculated medicament dose to the user.

A third aspect of the invention provides a method of operating a device, the method comprising:
  obtaining a parameter of a sample of body fluid from a user;
  using information provided by one or more sensors to calculate a measure of physical activity of the user;
  calculating a medicament dose using the measured parameter and the measure of physical activity of the user; and
  indicating the calculated medicament dose to the user.

BRIEF DESCRIPTION OF THE DRAWINGS

Embodiments of the invention will now be described by way of example with reference to the accompanying drawings, in which.

DETAILED DESCRIPTION

The following paragraphs will describe various embodiments of the invention. For exemplary purpose only, most of the embodiments are outlined in relation to a medical device or system and the respective method. Also, the detailed explanations given in the background of the invention section above are merely intended to better understand the constraints of an insulin treatment or a treatment with other hormones. Furthermore, the titration methods described herein can be applied to basal, premixed and mealtime insulin. In the following, the term insulin is used for all kinds of insulin and glargine unless otherwise stated.

Figure 1:
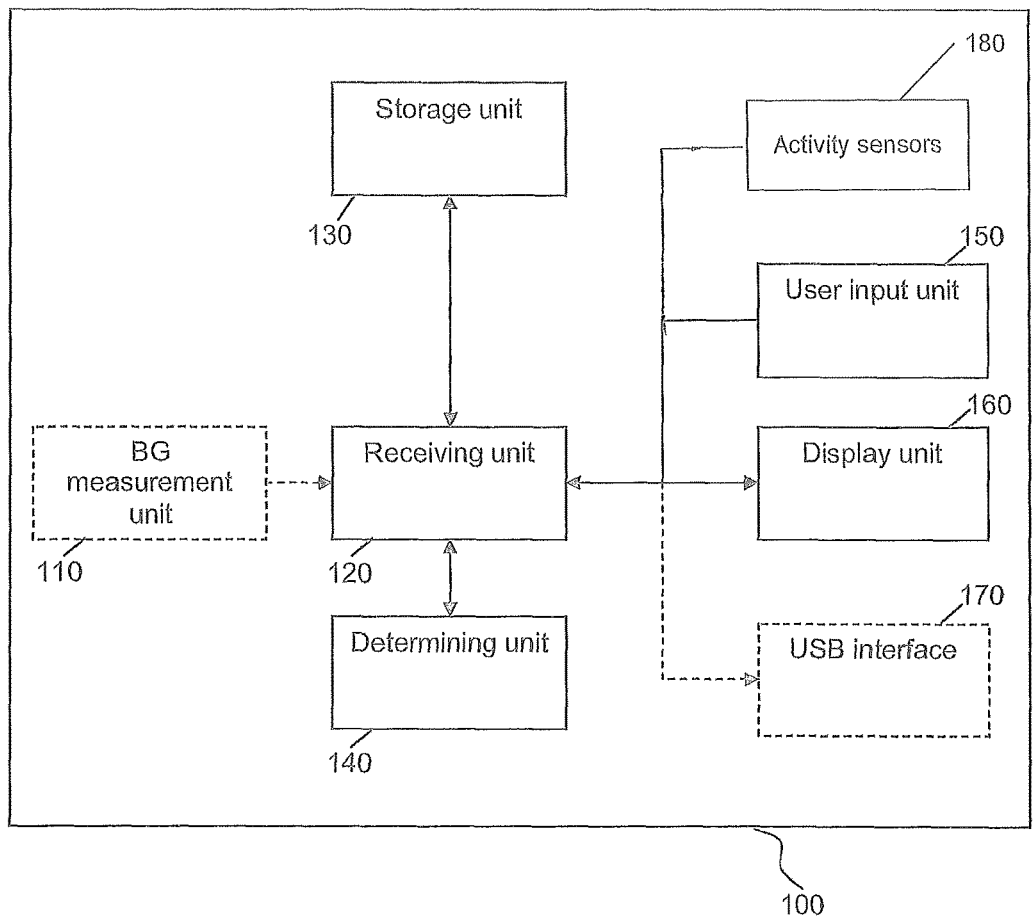
FIG. 1 is a schematic diagram of the medical device according to a preferred embodiment of the invention.

FIG. 1 is a schematic diagram of the medical device according to a preferred embodiment of the invention. The medical device 100 comprises a blood glucose measurement unit 110, which is arranged to measure the blood glucose level e.g. of the user of the medical device. The blood glucose measurement unit 110 is connected to a receiving unit 120, which is arranged to forward e.g. blood glucose value data received from blood glucose measurement unit 110 to a storage unit 130. Alternatively, the receiving unit may retrieve stored data such as e.g. blood glucose value data from the storage unit 130 and forward it to a determining unit 140. Alternatively, the receiving unit 120 directly forwards the blood glucose value data received from the blood glucose measurement unit 110 to the determining unit 140.

Receiving unit 120 is further connected to user input unit 150. The user input unit 150 is arranged to receive input from the user of the medical device 100. The user input data are forwarded from the user input unit 150 to the receiving unit 120, which either forwards it to the determining unit 140 or to the storage unit 130. Furthermore, the medical device 100 comprises a display unit 160, which is connected to the receiving unit 120. The display unit 160 receives data to be displayed from the receiving unit 120.

The medical device 100 may additionally comprise a further interface 170, such as a USB interface, an IRDA interface, Bluetooth interface, etc., in order to receive data and to transmit data. The interface 170 is connected to the receiving unit 120 in order to receive data from the receiving unit 120 and to forward data to the receiving unit 120.

The medical device 100 includes one or more activity sensors 180 connected to the receiving unit 120 in order to provide sensor data to the determining unit 140. The activity sensors 180 may include a pedometer that is configured to indicate a number of steps taken by the user. The activity sensors 180 may include an accelerometer, for instance a microaccelerometer, that provides output signals indicative of movement of the sensor 180 and thus the medical device 100. The one or more activity sensors 180 may instead take some other form. The one or more activity sensors allow the medical device 100 to obtain a measure of physical activity of the user.

As outlined above, the medical device 100 comprises a blood glucose measurement unit 110. Preferably, the blood glucose measurement unit 110 is arranged to measure the blood glucose level in the blood of e.g. the user by testing a drop of blood on a respective test strip. The measured blood glucose value is then transformed to blood glucose value data and forwarded immediately or on demand to the receiving unit 120. Alternatively, the blood glucose measurement unit 110 is arranged to measure the blood glucose level of e.g. the user via infrared diagnosis or an alternative contactless measurement method.

According to a further alternative the blood glucose measurement unit 110 is implanted in the body of the user of the medical device 100 and forwards the data to the receiving unit 120 either via a wired connection or via a wireless connection. Preferably, such an implanted blood glucose measurement unit 110 is a continuous measurement sensor e.g. based on a bio chip which allows a continuous closed loop control. In the latter case the blood glucose measurement unit 110 forwards the blood glucose measurement value data to the receiving unit 120 via interface 170. According to a further alternative the medical device 100 does not comprise a blood glucose measurement unit 110 which measures the blood glucose values, but receives blood glucose value data from an external unit.

The measurement of the blood glucose measurement is triggered by the receiving unit 120 which sends a respective signal to the blood glucose measurement unit 110. According to one preferred alternative the receiving unit 120 receives a trigger signal generated based on user input which is received via user input unit 150. Alternatively, the trigger signal is generated automatically by a timer unit or by determining unit 140. Preferably, the receiving unit 120 is represented e.g. by the input ports and output ports of a microprocessor or a bus system managing the data handling between several functional units. This includes bus systems, such as e.g. Advanced Microprocessor Bus Architecture bus systems implemented in a microprocessor or external bus systems connected to a microprocessor. Via the receiving unit 120, data are retrieved from the storage unit 130 on demand and forwarded to the determining unit 140, to the display unit 160 or to the interface 170. Moreover, the receiving unit 120 forwards signals, such as trigger signals or control signals e.g. to the blood glucose measurement unit 110, the display unit 160 or the interface 170.

The storage unit 130 is arranged to store data input via the user input unit 150, data received by the blood glucose measurement unit 110, data processed by the determining unit 140 and/or data received via interface 170. Furthermore, storage unit 130 is arranged to provide the stored data to the determining unit 140, to the display unit 160 and/or to the interface 170. The storage unit 130 is implemented as a semiconductor memory. Alternatively, it is implemented as a hard disk memory or an on-chip memory of the determining unit 140.

The determining unit 140 is a microprocessor or any other functional unit capable of processing data. The user input unit 150 may be implemented as one or more push buttons or alternatively as so called soft keys wherein the function of the respective soft key is displayed on the display unit 160. Alternatively, the user input unit 150 is a key board or a touch screen. Alternatively, the user input unit 150 comprises a microphone for receiving speech input so that data can be entered via speech input.

The display unit 160 comprises an LCD or LED display. Preferably, the display can display a number of alphanumerical characters so that e.g. the actual measured blood glucose value can be displayed together with additional instructions for the user. Alternatively, the display unit 160 comprises a graphic display in order to display graphs or graphics.

The interface 170 is a wireless interface, such as IRDA, Bluetooth, GSM, UMTS, ZigBee, or WI-FI, etc. Alternatively, the interface may be a wired interface, such as a USB port, serial port, parallel port, network card, etc., for receiving and transmitting data. The interface 170 may alternatively be omitted.

According to another alternative, the medical device 100 comprises, additionally to the interface 170, a chip-card reader or a chip-card reader interface. The chip-card reader is adapted to read a chip card, such as a SIM card or a chip card with information. For this, the chip card comprises a memory, wherein a selected algorithm together with corresponding parameters and a history of the blood glucose values and doses administered, etc. are stored. Thus, in the case that the medical device 100 has a defect, the relevant data can be easily removed from the medical device 100 via the chip card and transferred to a new medical device 100. Moreover, the chip card may be used in order to provide information on the history of the treatment to e.g. an HCP.

In the case that a SIM card is used together with the chip-card reader of the medical device 100 and the interface unit 170 is additionally a mobile communication interface, the basic functions of the medical device 100 can be unlocked by the provider of the SIM card via a telecommunication channel. This additionally offers the possibility that the medical device 100 can communicate with other telecommunication devices via predefined channels, such as UMTS or GSM. Via the international mobile subscriber identity, also called IMSI, stored in the SIM card, the medical device 100 identifies itself within a network and, thus, can be addressed via the network. In such a case the medical device 100 can be easily checked, remote controlled, updated, monitored, etc., by addressing the mobile communication unit e.g. with a phone number.

Furthermore, the medical device 100 is able to transmit data via SMS, e-mail or via mobile internet connection. Moreover, this offers the possibility to locate the medical device 100 in an emergency case.

The BG measurement unit 110 constitutes means for obtaining a parameter of a sample of bodily fluid from a user, for example a chemical or biological parameter of a sample of bodily fluid. The determining unit 140 constitutes means for using information provided by one or more sensors 120 to calculate a measure of physical activity of the user as well as means for calculating a medicament dose using at least in part the measured parameter and the measure of physical activity of the user. The determining unit 140 and the display unit 160 constitute means for indicating the calculated medicament dose to the user.

Figure 2:
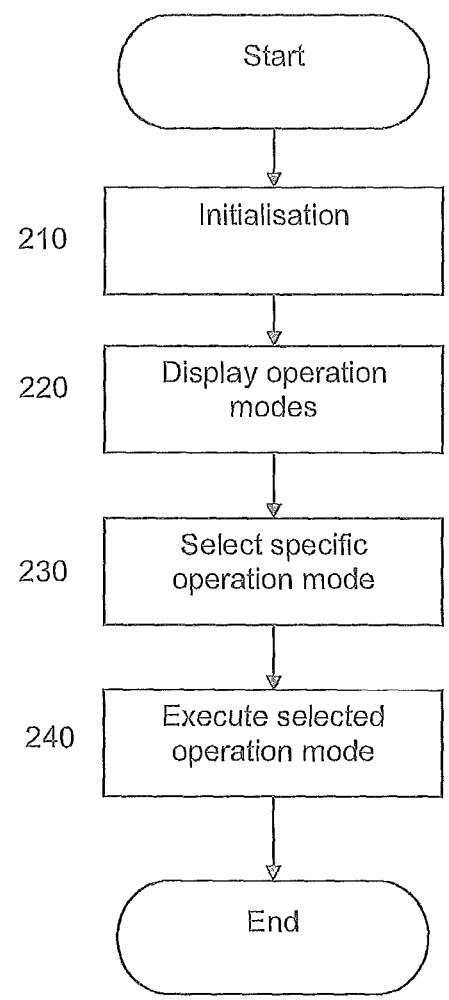
FIG. 2 is a flow diagram illustrating steps of operation of the medical device according to a preferred embodiment of the invention.

As shown in FIG. 2, the medical device 100 is capable to perform a number of operating processes. After switching on, the medical device 100 performs initialization step 210 for initializing the functional components of the medical device 100. After this, the different operation modes of which the medical device 100 is capable, are displayed in the display step 220. Preferably, modes such as "Measure BG", "Output insulin dose", "Mark event", "Review history" and/or "Change settings" can be displayed in step 220. In step 230 the user selects one of the displayed operation modes via the user input unit 150. In step 240 the selected operation mode is executed.

According to an alternative version of the operation process steps 220 and 230 may be skipped in the case that a specific operation mode is preselected. In that case, after initialization 210, the preselected operation mode, which is either preselected by the user or automatically selected in accordance with a specific event, the operating process proceeds with step 240 and executes the preselected one or more operation modes.

Depending on the operation mode, the operation process may continue after the execution of the selected mode with step 220 in order to give the user of the medical device 100 the option to choose a further operation mode or the operation process ends. In the latter case the medical device 100 is switched off automatically.

Figure 3:
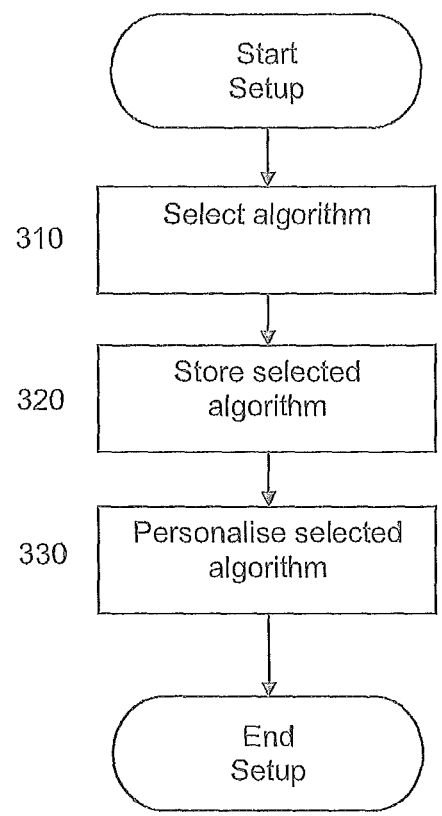
FIG. 3 is a flow diagram illustrating steps of a further operating procedure of the medical device according to a preferred embodiment of the invention.

One specific operation mode is the set up mode, which is also called change setting mode. FIG. 3 shows a schematic flow diagram of a preferred setup procedure.

As outlined above, the medical device 100 is adapted to measure a blood sugar level. Furthermore, it is arranged to review the history of the measured blood sugar. Preferably, the medical device 100 displays not only the recent blood glucose value data, but also the insulin dose administered. Moreover, the medical device 100 and in particular the determining unit 140 determine e.g. a dose of insulin to be administered based on specific parameters. Furthermore, the medical device 100 is arranged to receive data either via user input 150 or electronically via interface 170, which indicate specific events. Preferably, these functions or at least some of these functions can be adjusted to the needs of the user of the medical device 100. FIG. 3 shows such a setup procedure for customizing the functions of the medical device 100 to determine the dose to be administered.

As outlined above, a number of algorithms exists on how to determine the dose to be administered based on the FBG value and the dose administered recently. In order to optimize the functionality of the medical device 100, the setup procedure shown in FIG. 3 provides step 310 for selecting an algorithm appropriate for the optimal glycemic control of the user's blood sugar. In step 310 either a predefined algorithm is chosen or a new algorithm is defined. In step 320 the selected predefined or newly defined algorithm is stored or marked with an identifier, such as a flag or pointer, as the selected algorithm. Preferably, in a further step 330 the selected algorithm is further personalized. In the personalizing step 330 specific parameters of the selected algorithm can be further specified and/or selected in relation to the needs and requirements of the user of the medical device 100.

Details of the steps 310 to 330 are explained in more detail further below.

Figure 4:
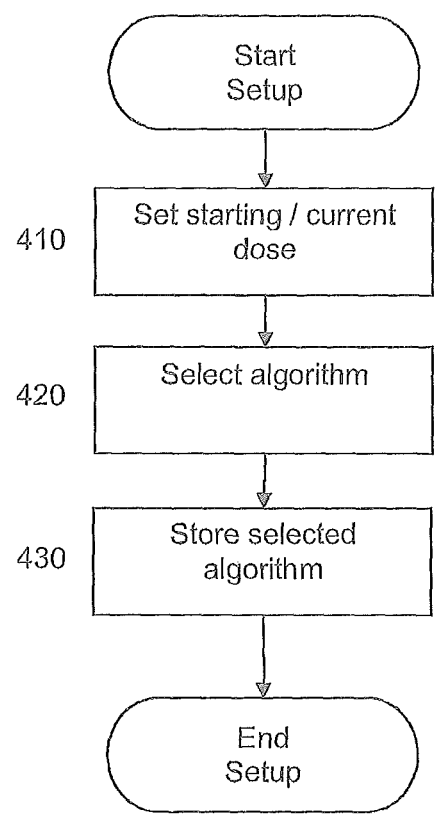
FIG. 4 is a flow diagram illustrating steps of another operating procedure of the medical device according to a preferred embodiment of the invention.

FIG. 4 shows an alternative way for setting up the algorithm for determining the dose to be administered. This alternative setup procedure refers to algorithms which provide fewer options to be personalized and, thus, provide more parameters which have been predefined. Accordingly, only a few parameters have to be adjusted in order to adapt the function for determining the dose to be administered to the needs and requirements of the user of the medical device 100. As shown in FIG. 4 in the alternative setup procedure, the starting dose or the current dose used by the user is input and stored in step 410. Preferably, the starting dose with which the user-directed titration is started is in the range of 10 to 20 units. Alternatively, in other cases lower or higher values are used. In the case that the user of the medical device 100 already uses a specific dose for obtaining appropriate glycemic control, this dose or a dose equivalent to another insulin type is chosen in step 410 as the current dose. In the latter case, preferably a safety approach is taken in which the starting dose is set as a lower dose than the dose equivalent to the other insulin type.

In step 420 a suitable algorithm is chosen and the algorithm is then stored in step 430. As outlined before, storing of the selected algorithm does not necessarily require that the selected algorithm is stored additionally in the storage unit 130. Instead, the selected algorithm may be identified with an identifier such as a pointer or a flag which is stored in the storage unit 130 in relation to the selected algorithm.

Figure 5:
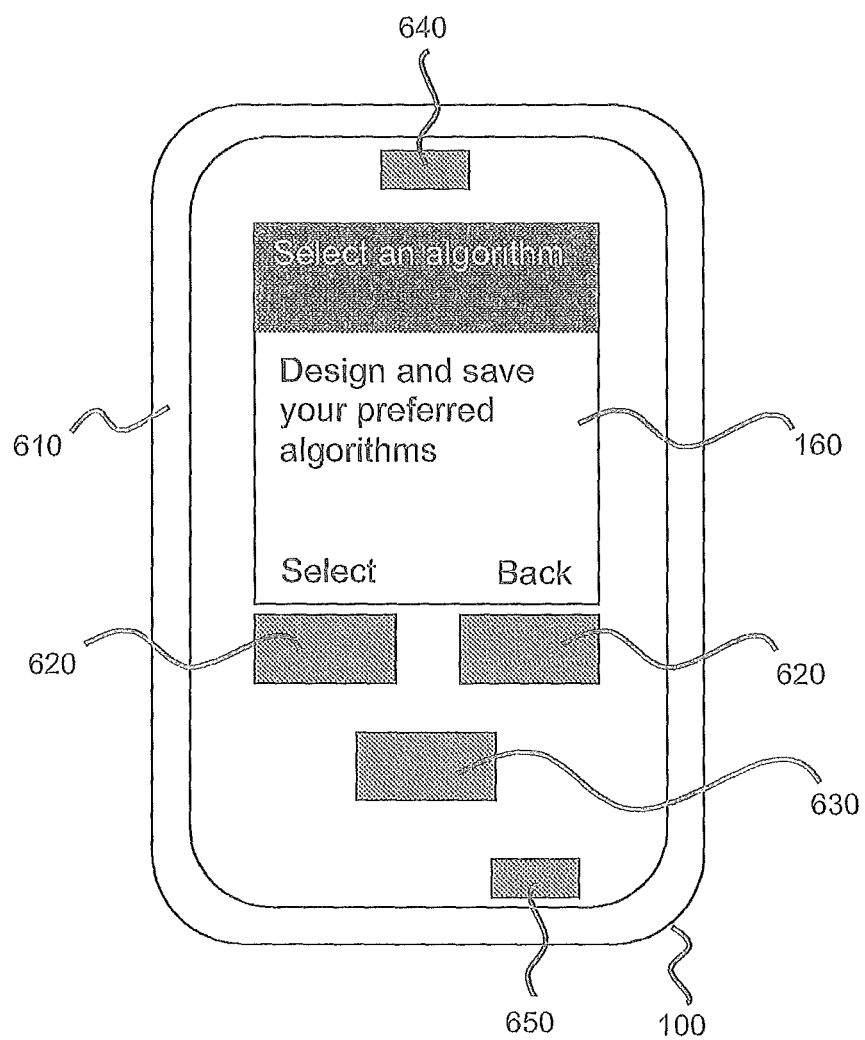
FIG. 5 is another schematic diagram of the medical device shown in FIG. 1.

Further configuration options for personalizing the process for determining the dose to be administered may be provided, as described in WO 2010/089307, FIG. 5 of which and the related description are herein incorporated by reference.

FIG. 5 shows a further schematic diagram of the medical device 100 according to a preferred embodiment of the invention. In particular, FIG. 5 shows details of the housing and the display of the medical device 100 according to a preferred embodiment of the invention. The medical device 100 comprises housing 610 wherein in the upper side of the housing 610 the display unit 160 is placed. Next to the display unit 160, the housing 610 shows a section wherein soft keys 620 and a navigation key 630 are placed. The soft keys 620 are placed directly next to the display, preferably to the lower left and lower right side of the display. Thus, the display can show the function actually assigned to the soft keys 620. Preferably, a soft key is a button located alongside the display unit 160. This soft key performs the function dependent on the text shown near it at the moment on the display.

The navigation key 630 is used for scrolling through the menu selections displayed in the display unit 160. Preferably, by pressing the upper part of key 630, one can scroll up the menu selections and by pressing the lower part of key 630, one can scroll to the lower part of the menu selections. Correspondingly, by pressing the left part of key 630, one can scroll to menu selections on the left side and when pressing the right part of key 630, one can scroll to the right part of the menu selections. By pressing the centre of the key 630, one can select the chosen menu selection. Alternatively, a navigation pad or a touch screen is used for navigation.

Preferably, medical device 100 comprises a loudspeaker 640 connected to an acoustic module for outputting acoustic signals such as acoustic alerts or speech. Moreover, the medical device 100 also comprises a microphone 650 for speech input, voice recognition or for communicating via a network connection.

Figure 6:
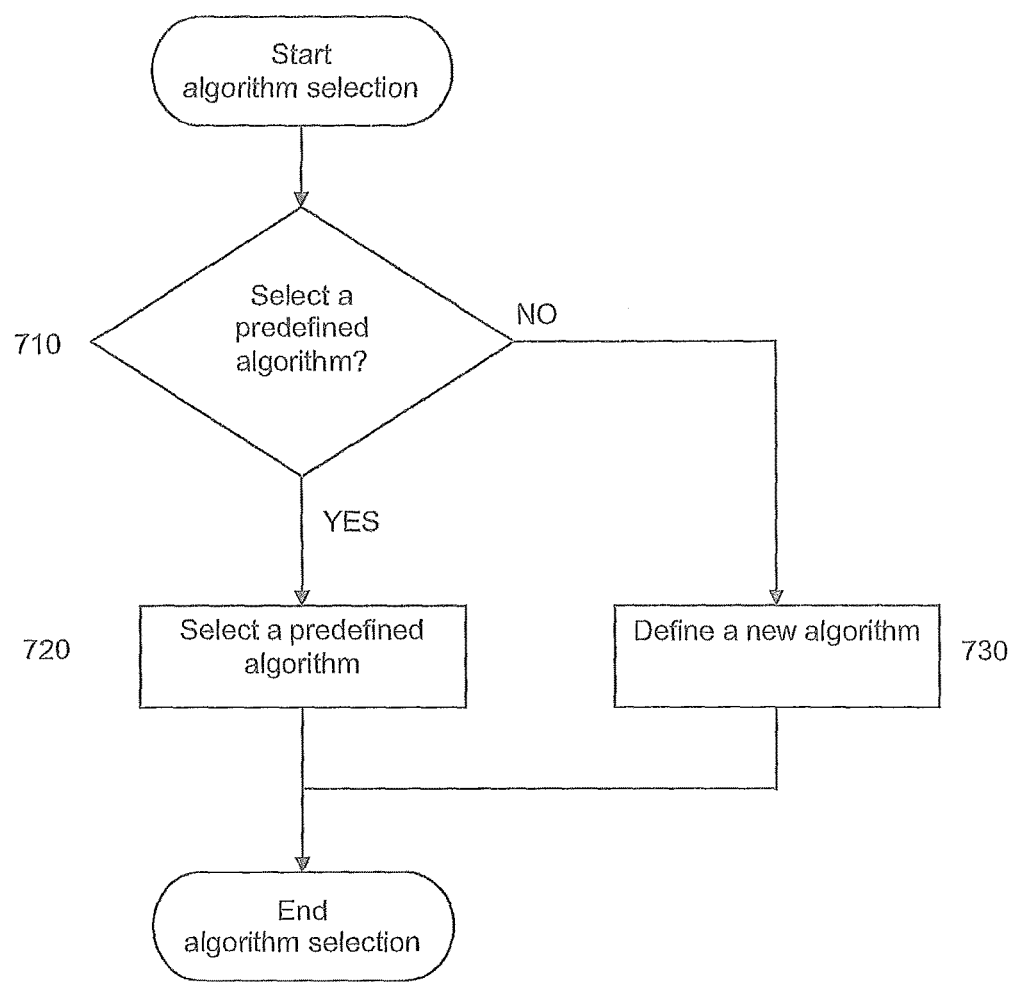
FIG. 6 is a flow diagram illustrating steps of the operating procedure shown in FIG. 3 in further detail.

FIG. 6 shows a flow diagram illustrating the steps of the operating procedure for selecting an algorithm as shown in FIG. 3 in step 310. If it is decided in step 710 of the algorithm selection procedure to select a predefined algorithm, it is proceeded to step 720 in which a predefined algorithm is selected. In the case that it is decided not to select a predefined algorithm, but to define a new algorithm, the method proceeds with step 730. Step 720 may also include the selection of low FBG rules, hypoglycemic rules and further intervention rules. The substeps for defining a new algorithm are explained in further detail in regard to FIG. 9.

Figure 8:
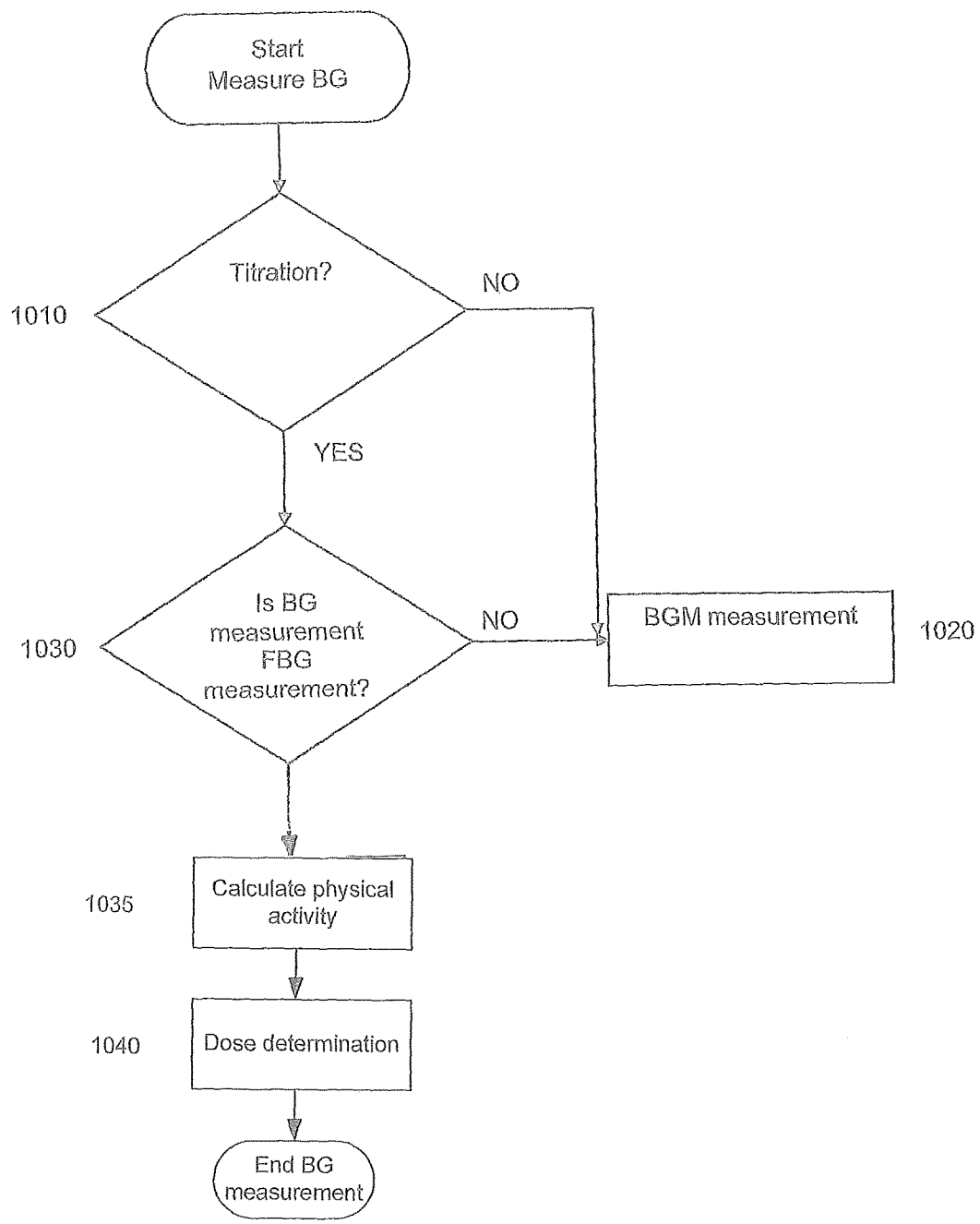
FIG. 8 is a flow diagram illustrating steps of the operation procedure shown in FIG. 2 in more detail.
Figure 9:
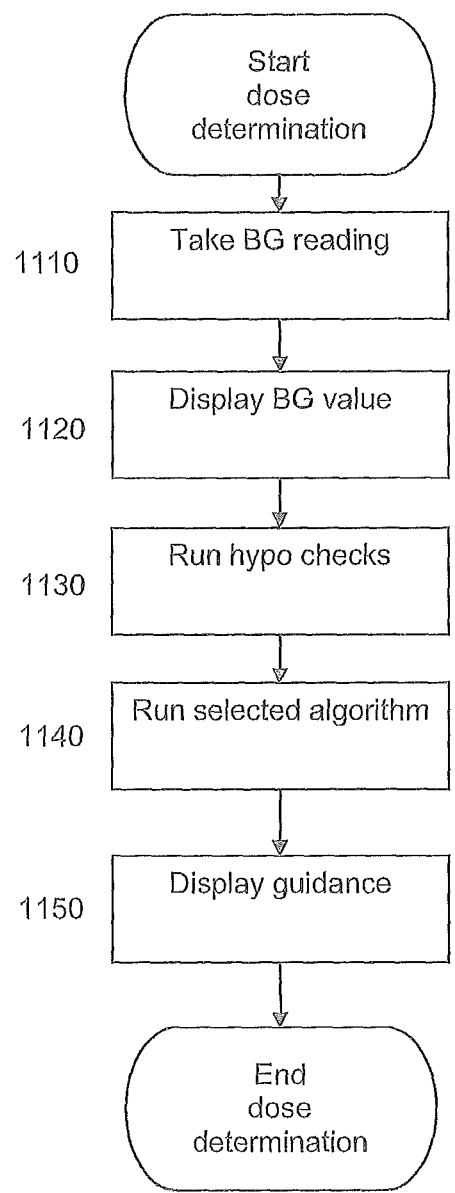
FIG. 9 is a flow diagram illustrating steps of the operating process as shown in FIG. 8 in more detail.

Further details of selecting and personalising an algorithm are described in WO 2010/089307 with reference to FIGS. 8 and 9, which along with the related description are incorporated herein by reference.

The medical device 100 is configured to monitor physical activity of the user. This is achieved by the determining unit 140 analysing outputs of the one or more activity sensors 180 and storing representative data in the storage unit 130.

To ensure that the medical device 100 monitors all activity of the user, either the medical device 100 is active continually or alternatively is able to be woken from a sleep mode when activity occurs. This can be achieved using the one or more activity sensors 180 themselves, particularly in the case of a gyroscope or accelerometer sensor. Waking of the medical device 100 from sleep mode when movement of the device is detected can be performed in any suitable way, for instance similarly to wakening in response to detection of movement used in some mobile phones, tablet computers etc.

When activity is detected, the determining unit 140 is configured to store in the storage unit 130 information identifying the intensity of physical activity over time.

Figure 7:
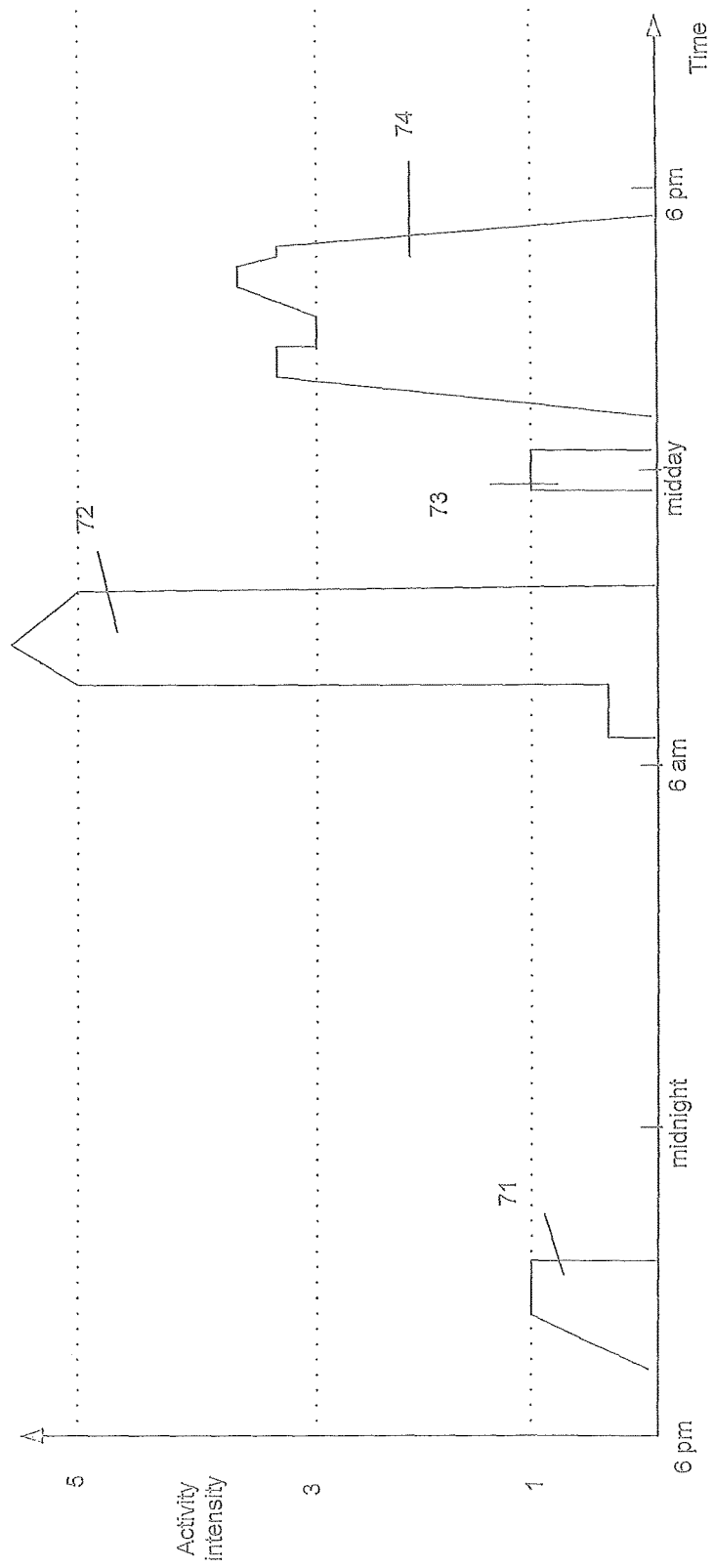
FIG. 7 is a diagram illustrating detected physical activity plotted as activity intensity over a period of time.

Referring to FIG. 7, data stored in the storage unit 130 by the determining unit 140 based on outputs of the one or more activity sensors 180 is illustrated. Here, time is shown on the horizontal axis and activity intensity is shown on the vertical axis. The period shown in FIG. 7 is from 6 pm on one day to 6 pm on the following day, although this is purely illustrative. FIG. 7 is a graphical illustration of the data stored in the storage unit 130. It shows that a first period 71 of relatively low intensity activity occurred from 7 pm to 8 pm. This first period 71 is shown to have a gradual increase from rest to a certain activity intensity, where the intensity remains the same for a period of time until the activity intensity reduces to zero relatively quickly. The period of activity 71 might for instance be representative of the user taking a walk.

A second period of activity 72 is shown to start soon after 6 am. Here, a relatively short period of relatively low intensity activity is followed by a period of relatively high intensity activity. The transition from rest to low intensity is relatively quick, and the transition from low intensity activity to high intensity activity also is relatively quick. During the part of relatively high activity intensity, the intensity rises gradually to a peak then gradually falls again, before activity is stopped relatively quickly at approximately 8 am. The second period of activity 72 may be indicative for instance of the user walking to the gym then performing some intense physical exercise, for instance running on a treadmill or using an exercise bike.

A third period of activity 73 occurs around midday. This is shown in FIG. 7 to be relatively short in duration.

Soon after the third period of activity 73 ends, a fourth period of activity 74 begins. This is shown to increase relatively gradually from rest to a relatively medium level of intensity, whereupon the intensity fluctuates for a period of approximately two hours before the intensity relatively quickly falls back to rest. The fourth period of activity 74 might be indicative of the user undertaking some hill walking, a long cycle ride, or horse riding, for instance.

The determining unit 140 may determine an intensity of activity undertaken by the user in any suitable way. In the case of the one or more activity sensors 180 including an accelerometer or microaccelerometer, the intensity of activity can be derived by the determining unit 140 by integrating the magnitude of the output of the accelerometer over time. The output of the accelerometer 180 may be integrated over a period of some tens of seconds, for instance 30 seconds or 1 minute.

In the case of the one or more activity sensors 180 including a heart rate detector, the intensity of the activity may simply be recorded as the elevation of the user's heart rate above their rest heart rate, or it may be provided using some more sophisticated calculation. Providing a measure of activity intensity for a blood pressure sensor 180 can be performed in a similar way. The use of a heart rate monitor in conjunction with a blood pressure detection device as the activity sensors 180 can provide a more reliable indication of intensity of activity undergone by the user.

In the case of a pedometer constituting the one or more activity sensors 180, the activity intensity may be derived from a step rate of the user. Here, a low step rate may indicate walking, and therefore be interpreted by the determining unit 140 as relatively low intensity activity. A medium step rate may indicate slow jogging by the user, and a medium intensity activity inferred by the determining unit 140. A high step rate may indicate fast jogging or running by the user, and the determining unit 140 may infer a relatively high intensity activity therefrom.

The determining unit 140 is configured to determine a level of intensity of activity in each of plural consecutive time periods and to record the intensity information along with an indication of the associated time period in the storage unit 130. For instance, the determining unit may determine activity intensity for periods of tens of seconds, 30 seconds, 1 minute or 2 minutes, and record the result in data in the storage unit 130. The smaller the time interval that is used by determining unit 140, the greater is the resolution of activity intensity monitoring and thus the more representative is the data of the users activity. However, relatively small monitoring periods results in a larger amount of data being stored in the storage unit 130. Thus, a relatively small monitoring period requires the storage unit 130 to comprise more memory. A larger interval, conversely, allows a smaller storage unit 130 to be used.

As outlined above, the medical device 100 also provides the function for measuring the blood sugar level, preferably in the blood of the user. The medical device 100 also provides the function for measuring physical activity undergone by the user. The measurement of the blood sugar level, also called blood glucose value, and the measure of physical activity is combined with the dose determination procedure as shown in FIG. 8.

The blood glucose measurement procedure starts with a detection of whether the medical device 100 is in a titration mode or not. This detection is performed in step 1010. Whether the medical device 100 is in a titration mode or not is preferably detected automatically via parameters stored in the storage unit 130 or determined by the determining unit 140. Preferably, such a parameter is the titration interval or the time of day. In the case that the parameter is the titration interval and the titration interval is, for example three days, the medical device 100 is automatically in the titration mode if the last titration has been three days ago. Alternatively, if the titration is based on the FBG value and, thus, the titration is performed in the morning, the medical device 100 is in the titration mode every morning. According to a further alternative, the medical device 100 is switched automatically to the titration mode based on a combination of both parameters, such as titration interval and time of day. In such a case, the medical device 100 is automatically switched to the titration mode if the titration interval has passed and when the time of day is when the titration is usually performed.

Alternatively, if no FBG value is measured the dose recommendation is given based on the previous FBG value and based on the previous measured or reported other blood glucose values. Preferably, a dose guidance is given even if no actual FBG value is available as long as this function is activated. According to another alternative, the medical device 100 is switched to the titration mode manually via user input through the user input unit 150 or via input through interface 170.

In the case that the medical device 100 is not in the titration mode, the blood glucose measurement procedure proceeds to step 1020 in which the blood glucose value is measured. This blood glucose measurement step 1020 includes that the blood glucose value is determined and transformed to a blood glucose value data which is forwarded to the storage unit 130 and stored in relation with the time and date indicating when the measurement has been made. Optionally, the user may mark this blood glucose value data as FBG value data or other blood glucose value data.

In the case that the medical device 100 is in the titration mode, then the blood glucose measurement procedure proceeds to step 1030, in which it is detected, whether the measurement is a FBG measurement or any other blood glucose measurement. Preferably it is automatically detected whether or not the blood glucose measurement is a FBG measurement. Preferably, this detection is based on the time of day. In the case that the FBG measurement is usually performed in the morning, the medical device is automatically switched to the FBG measurement mode if the blood glucose measurement procedure is performed at morning time. Alternatively, the FBG measurement mode is detected via other parameters or defined via user input. In the latter case, the user is requested to select the respective mode. In the case that the medical device is not in the FBG measurement mode, the blood glucose measurement procedure proceeds to step 1020. In the case that the medical device 100 is in the FBG measurement mode, the blood glucose measurement procedure proceeds to step 1040 for determining the dose to be administered.

In the case that the determination of the dose to be administered is based on the measurement of the FBG value, the blood glucose measurement procedure proceeds to the physical activity calculation step 1035.

At step 1035, a measure of physical activity of the user is calculated. Step 1035 of FIG. 8 involves the determining unit 140 reading the data from the storage unit 130 that was provided by the determining unit 140 based on the data provided by the one or more activity sensors 180. Step 1035 may involve disregarding data that is not relevant to those calculations. For instance, it may involve disregarding data that is sufficiently old that it is not significant to the dose of insulin required by the user. It may also involve disregarding data that relates to times prior to the last insulin administration, since that physical activity might be considered to have been accommodated already in the user's medication.

Step 1035 may involve processing the data that is not disregarded in any suitable way. For instance 1035 may involve simply calculating the sum of the product of activity intensity and duration, or put another way calculating the area under the graph in FIG. 7. This is simple to achieve, but the resulting measure of psychical activity may be less useful than measures provided through more sophisticated calculations.

Alternatively, step 1035 may involve summing the product of activity intensity with respect to time, however weighting the products so that higher intensity activities are given more prominence. For instance, high intensity activities such as running may be weighted so as to cause them to contribute to more to the output measure than would result from the simple indication of activity intensity provided by the data stored in the storage unit 130.

Alternatively or in addition, a higher weighting may be given to more recent exercise. Using the example of FIG. 7, for instance, the fourth period of activity 74 may be weighted such that a measure provided by the step 1035 incorporates a larger contribution by the fourth period activity 74 compared to the second period of activities 72 even having regard to the areas under the graphs of those periods of activity.

Instead of step 1035 producing a single measure of physical activity, is may provide plural measures. For instance, it may provide a first measure for the second period of activity 72, a second measure for the third period of activity 73 and a third measure for the fourth period of activity 74. The separate measures may include a measure of the physical activity and an indication of the time at which the activity occurred. For an extended period of activity, such as the fourth period of activity 74, this may indicate the start time, end time or a central time.

After the measure of physical activity has been calculated, the operation proceeds to a dose determination step 1040. In dose determination step 1040, a dose to be administered is proposed. At step 1040, the dose determination is performed using the measure of physical activity provided by step 1035. The exact algorithm is not described here because it will be appreciated to the skilled person how to incorporate user physical activity information into a dose determination in order to calculate a dose of insulin that would be of the highest benefit to the user's health. The user may be asked whether the proposed dose should be maintained or changed to a different value.

As already indicated above, if the FBG measurement was not carried out because it was forgotten or skipped for any reasons, a dose guidance may be given nevertheless, for example if only a single measurement was not carried out after a long series of measurements, and if the series of measurements didn't show any levels of hypo- or hyperglycemia. A dose recommendation for the dose to be administered may be given based on the previous FBG value or previous FBG values and based on the previous measured or reported other blood glucose values.

The substeps of the dose determination step 1040 are illustrated in more detail in FIG. 9.

FIG. 9 is a flow diagram illustrating the substeps of the dose determination procedure. In step 1110, the blood glucose level is measured and the corresponding blood glucose value determined. Preferably, the respective blood glucose value data is stored in the storage unit 130 together with the time and date when the blood glucose measurement was performed. As the blood glucose measurement is a FBG measurement, the stored value is automatically marked as a FBG measurement value.

In step 1120, the measured blood glucose value is displayed on the display unit 160, preferably together with the time and date when the measurement was performed. Additionally, it is also displayed on the display unit 160 that the blood glucose value is a FBG value. Moreover, the blood glucose value is displayed in units of mg/dl or mmol/l.

Either automatically after a specific predetermined time interval or depending on a user input, the dose determination procedure proceeds to step 1130, in order to run hypoglycemic checks. These hypoglycemic checks will be explained in more detail further below. In the case that the hypoglycemic checks performed in step 1130 do not come to a negative result, the dose determination procedure proceeds to step 1140. In step 1140, the selected algorithm is executed for determining the dose to be administered. When the dose to be administered has been determined in step 1140, guidance is displayed in step 1150. Preferably, this guidance includes information about the most recent FBG values and the actual FBG values together with the respective administered doses. Furthermore, the displayed guidance includes information about the actual dose to be administered. The guidance displayed will be explained in more detail further below in context with FIG. 10. In the case that the dose determined in step 1140 is accepted by the user, the dose is stored in relation to the time and date when determined in the storage unit 130. In the case that the medical device 100 comprises a dose setting unit and a dose delivering unit, data representing the dose determined, are transmitted to the dose setting unit. Alternatively, data representing the dose to be administered are transmitted to an external dose setting unit and dose delivering unit.

Figure 12:
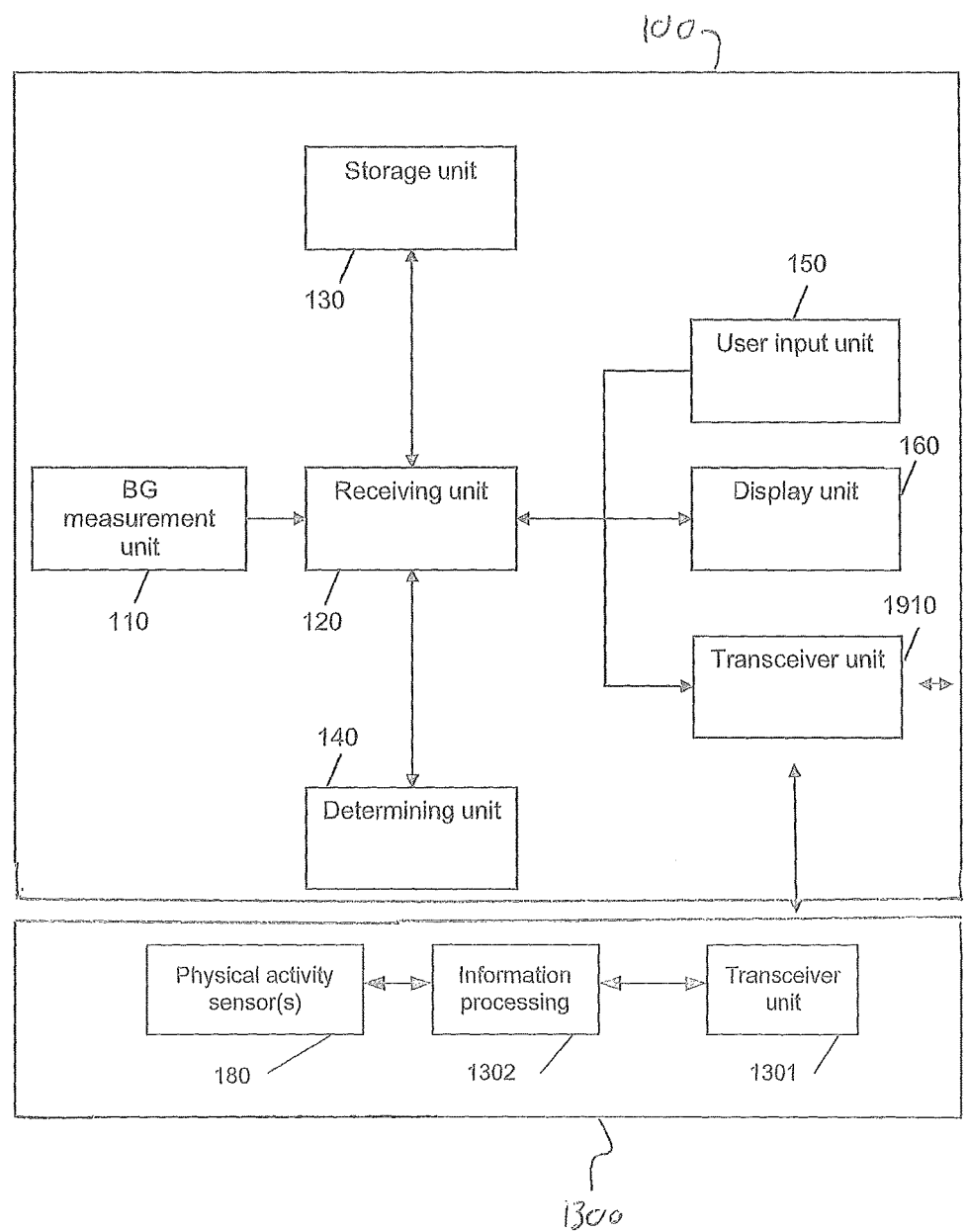
FIG. 12 is a schematic diagram illustrating the medical device according to another preferred embodiment of the invention.

Substeps of the hypoglycemic checks procedure are described in WO 2010/089307 with reference to FIG. 12, which along with the related description is incorporated herein by reference.

Figure 13:
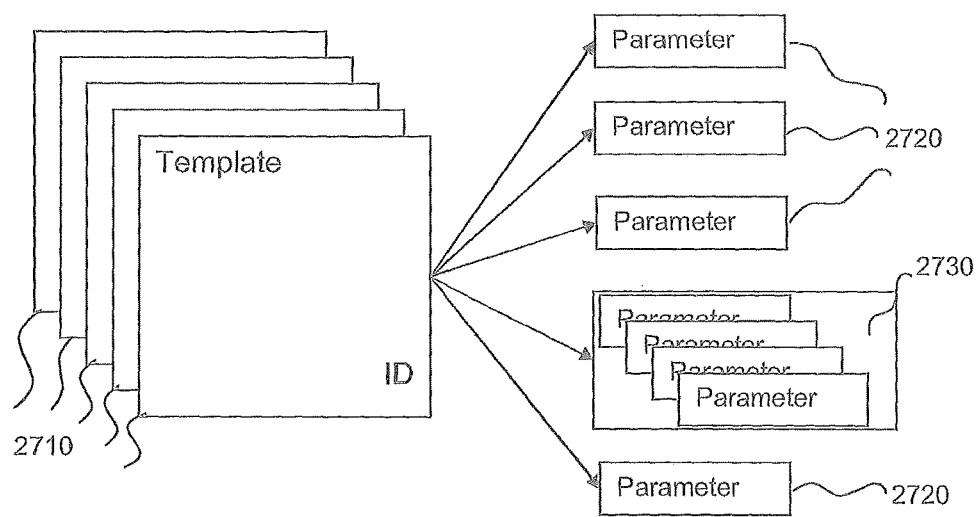
FIG. 13 is a schematic diagram illustrating the relation of the templates with the parameters and parameter sets according to embodiments of the invention.

An alternative version of the blood glucose measurement procedure shown in FIG. 8 is described in WO 2010/089307 with reference to FIG. 13, which along with the related description is incorporated herein by reference.

Figure 10:
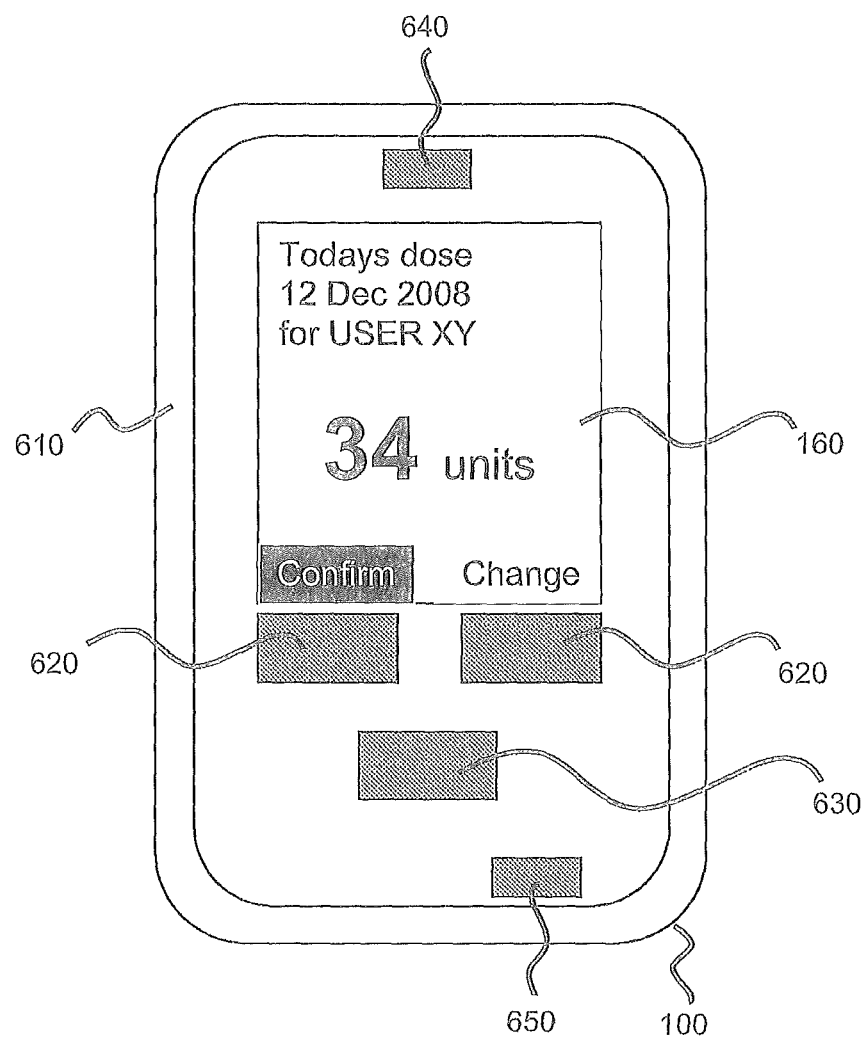
FIG. 10 is another schematic diagram of the medical device shown in FIG. 1.

FIG. 10 is a schematic diagram showing the display of the medical device 100 for an operation mode, as explained in context with step 1150. The display unit 160 displays the guidance for the user. Preferably, this is the dose to be administered. As shown in FIG. 10, the functions "confirm" and "change" are assigned to the soft keys 620, so that the user of the medical device 100 can accept the dose determined in step 1140 or can change it. Alternatively, not only the determined dose is displayed but also the previously administered doses together with the corresponding measured FBG values. Thus, the user of the medical device 100 has additional information for deciding, whether to accept the determined and displayed dose or not. Moreover, personalization information is displayed in the display unit 160, such as the user name, so that the user can easily identify that the dose has been determined based on the algorithm and parameters selected and personalized for the user.

In the case that the medical device 100 is connected via a wired or wireless interface to an external dose setting unit, the user is requested whether data corresponding to the displayed units for the dose to be administered shall be transmitted to the dose setting unit. In the case that the user confirms the transmission, respective data corresponding to the displayed dose are transmitted to the dose setting unit.

Alternatively, all information displayed on the display unit 160 is output via a voice module. The output via the voice module is triggered via a user input. Alternatively, the output via voice module is performed automatically based on a user selection in a setup menu. According to a further alternative version, the information displayed on the display is transmitted to a headset, for instance via Bluetooth.

Figure 11:
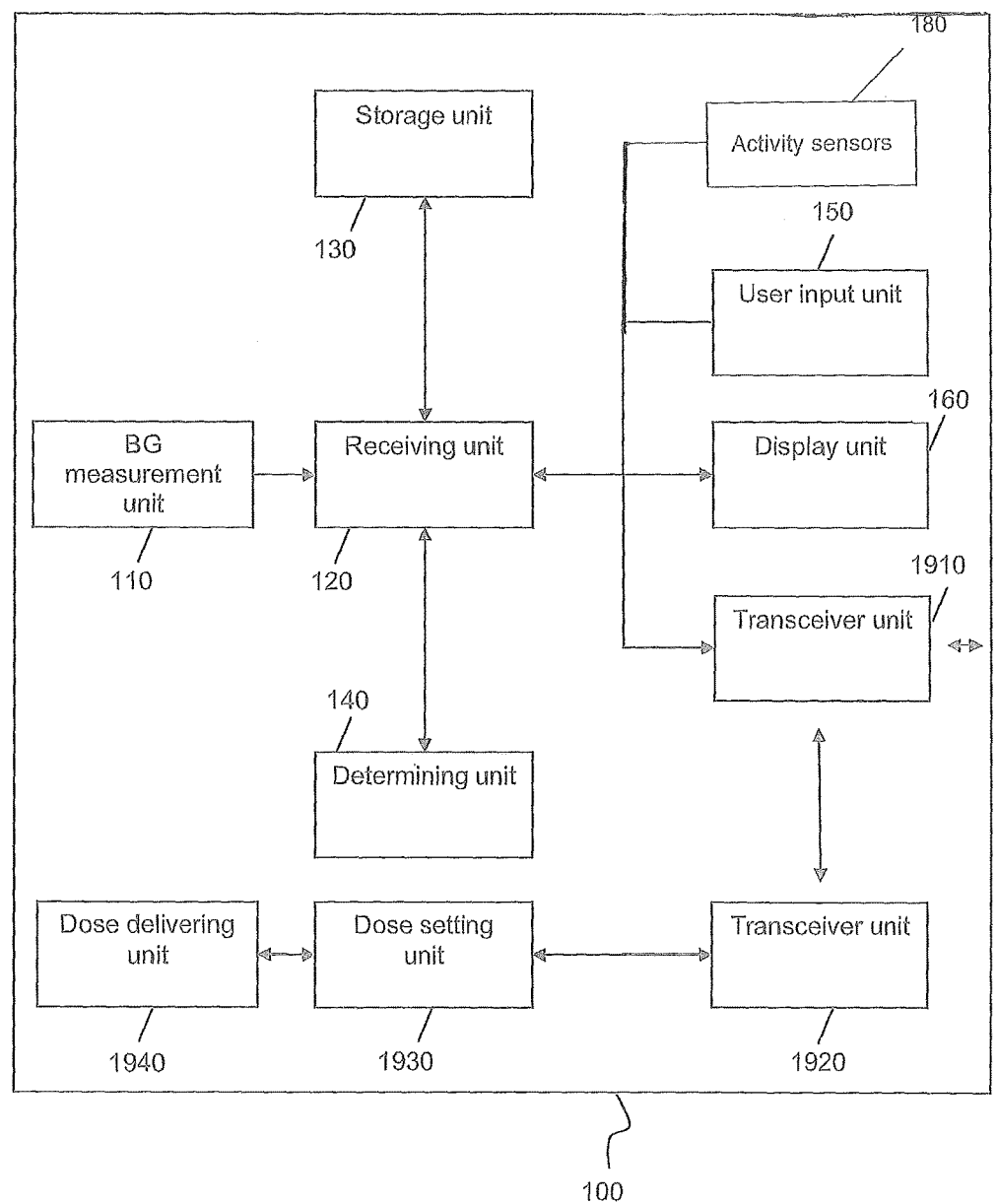
FIG. 11 is a schematic diagram illustrating the medical device according to another preferred embodiment of the invention.

FIG. 11 is a schematic diagram illustrating the medical device 100 according to a further preferred embodiment of the invention. The medical device 100 comprises a blood glucose measurement unit 110, a receiving unit 120, a storage unit 130 and a determining unit 140. Additionally, the medical device 100 comprises a user input unit 150 and a display unit 160, as already shown in FIG. 1. Additionally, the medical device 100 shown in FIG. 11 comprises a transceiver unit 1910 capable to communicate, preferably wirelessly, with additional internal and external components. Furthermore, the medical device 100 comprises a further transceiver unit 1920 capable to communicate with the transceiver unit 1910. The transceiver unit 1920 is connected to a dose setting unit 1930 for setting a dose to be administered according to the signals received from the transceiver unit 1920. The dose setting unit is further connected to a dose delivering unit 1940. Preferably, the transceiver unit 1920, the dose setting unit 1930 and the dose delivering unit 1940 form a functional and structural unit which is separated from the other components shown in FIG. 11. Preferably, the transceiver unit 1920, the dose setting unit 1930 and the dose delivering unit 1940 form an insulin pen or insulin pump or an inhaler device which receives signals from the transceiver unit 1910 which dose has to be set in order to deliver a dose determined by the determining unit 140. If the transceiver unit 1920 receives the respective signals for setting a dose, the dose setting unit 1930 activates the respective dose setting mechanism for setting the dose according to the received signals. The delivery of the dose to be administered is either activated manually by the user of the medical device 100 or automatically activated. In the case of an insulin pen the activation is preferably done manually by the user. In the case of an insulin pump the activation is preferably done automatically. According to a preferred alternative the dose delivering unit 1940 forwards a signal to the transceiver unit 1920 that the dose set has been successfully delivered. Accordingly, the transceiver unit 1920 transmits the respective signal of the successful delivery of the dose set to the transceiver unit 1910. Thus, the successful delivery of the set dose can be protocolled by the determining unit 140 and stored in the storage unit 130.

In the case that the blood glucose measurement unit 110 is a continuous sensor which is e.g. implanted and the dose delivering unit 1940 is an insulin pump an automatic delivery system is provided. In the case that this full automatic delivery system asks for a user confirmation in the case of a dose increase a semi closed loop control is provided.

In the embodiments described above, the one or more activity sensors 180 are integrated into the medical advice 100. In alternative embodiments, one of which will now be described with reference to FIG. 12, the one or more physical activity sensors 180 are incorporated into a device 1300 that is external to the medical device 100.

The external device 1300 includes a transceiver unit 1301 that is operable to communicate with the transceiver unit 1910 of the medical device 100. The transceiver unit 1301 may take any suitable form, as described above with reference with respect to the transceiver unit 1920 of FIG. 11.

The external device 1300 also includes an information processing unit 1302. The output of the one or more activity sensors 180 are connected to the information processing unit 1302. The information processing unit 1302 is configured to analyse the data provided by the physical activity sensors 180 and provide information indicative of the activity of the user for transmission to the medical advice 100 by the transceiver unit 1301. This results in less data being needed to be transmitted by the transceiver unit 1301, and also requires less processing by determining unit 140 of the medical device 100. The information processing unit 1302 may be configured to indicate the intensity and time of activity performed by the user in the same way as described above with reference to FIG. 7, for instance.

The external device 1300 may for instance take the form of a sports watch. This may include an accelerometer as one of the one or more physical activity sensors 180. The sports watch 1300 may additionally include a heart rate monitor as one of the physical activity sensors 180.

In other embodiments (not shown in the Figures), the external device 1300 includes one type of physical activity sensor 180 and the medical device 100 includes another type of physical activity sensor 180. For instance, the external device 1300 might include a heart rate monitor 180 and the medical device 100 might include an accelerometer 180. In such an embodiment, the information processing unit 1302 processes the output of the heart rate monitor 180 in the external device 1300 and provides indicative information to the medical device 100 via the transceiver unit 1301. The determining unit 140 than processes this information in conjunction with accelerometer information provided by the accelerometer 180 in the medical device 100 to produce data indicative of activity undertaken by the user for storage in the storage unit 130.

The external device 1300 may alternatively take the form of an exercise machine, for instance a treadmill or exercise bike. The physical activity sensors 180 and the information processing unit 1302 of the external device 1300 may then provide output information in the form of work done by the user and/or power at each of multiple instances of time. Such information can be used by the determining unit 140 to indicate more closely a level of activity undertaken by the user. The physical activity sensors 180 and the information processing unit 1302 of the external device 1300 is this instance can be described as an ergometer.

The external device 1300 may alternatively include a pedometer as the activity sensor 180. In this case, the processing required by the information processing unit 1302 is relatively low.

The external device 1300 may provide activity information to the medical device 100 as the activity is happening, or it may be transferred periodically, at the end of the period of activity or in response to a user input. In the case of the transceiver unit 1301 or the transceiver unit 1910 being a wired unit, e.g. a USB module, information is transferred only when the transceiver units 1301, 1910 are physically connected together.

The medical device 100 is configured to verify that information received from the external device 1300 relates to a user that is registered with the device. The medical device 100 is configured to disregard information other than verified information when calculating the medicament dose.

In addition to using the information about the physical activity of the user in the dose determination step 1040 of FIG. 8, this information can be provided to the user and/or an HCP. For instance, the medical device 100 may be configured to show on the display unit 160 the amount of activity completed by the user in the current day. This may be indicated on an absolute level, or may be indicated as a percentage of a target for the user. For instance, the medical device 100 may display on the unit 160 after the second period of activity 72 that the user has achieved 80% of their target activity for the day. After the forth period of activity 74, the determining unit 140 may cause to be displayed on the display unit 160 an indication that the user has achieved 145% of their target activity for the day. Achievement of the target may be accompanied by a reward, for instance a smiley icon or similar.

Data indicating the physical activity of the user may be communicated to an HCP's device or computer along with other information such as insulin doses, times of administration etc. Preferably, the algorithms or dose adjustment profiles are based on several components, such as templates and parameters. Preferably, algorithms are composed by one or more templates and one or more parameter sets. FIG. 13 is a schematic diagram illustrating the relation of the templates with the parameters and the parameter sets according to a preferred embodiment of the invention.

Preferably, the medical device 100 comprises a set of templates 2710, which are already predefined. Each template 2710 comprises an ID, which uniquely identifies the template. Furthermore, each template comprises one or more parameters 2720 and/or one or more parameter sets 2730. These parameters are also identified via a unique identifier. Preferably, the relation between the template ID and the parameter IDs and parameter set IDs is stored.

Moreover, different templates are provided for different sections of the algorithm. Preferably, specific templates are provided for starting the algorithm, for the different phases of the algorithm, for terminating the algorithm, for low FBG rules, for hypoglycemic rules and for intervention rules. By composing the different templates via selecting one or more of the specific template a new algorithm can be composed, which comprises the startup of the algorithm, the different phases of the algorithm, the termination of the algorithm together with the low FBG rules, the hypoglycemia rules and the further intervention rules. Furthermore, the templates comprise predefined actions, such as displaying a set of parameters from which a specific parameter has to be selected for personalization, for requesting a value to be input by the user, for displaying a number of checkboxes, which have to be marked by the user, etc. Accordingly, the templates for initializing the algorithm comprise a drop-down menu from which the starting value or current value of the dose is selected or offer a request to the user to enter the value manually. The template for the different phases of the algorithm comprise a drop-down menu or a request for manual input of the titration interval and the dose increase, which is made for each titration interval.

Preferably, the parameter and parameter sets define a specific initial dose value, a specific first dose increase step, a specific first time interval for increasing the dose, a specific first target blood glucose value, a specific second dose increase step, a specific second time interval for increasing the dose, a specific second target blood glucose value, etc., a specific low blood glucose threshold value, a specific low blood glucose dose decrease step, a specific hypoglycemic blood glucose threshold value, a specific hypoglycemic blood glucose dose decrease step, etc.

The templates for the rule comprise a list of rules and actions, which are executed in the case that a specific event occurs. This also includes the input of information, such as e-mail addresses to which e.g. an alert is sent.

It will be appreciated that the above described embodiments are purely illustrative and are not limiting on the scope of the invention. Other variations and modifications will be apparent to persons skilled in the art upon reading the present application. For example, although the invention has been described with respect to a blood glucose meter and to calculation of doses of insulin, the teachings herein are applicable to the measurement of parameters of other bodily fluids, such as plasma, tears or saliva, and calculation of doses of other medicaments. Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. A device comprising:
   a blood glucose measurement unit configured to obtain a glucose level of a sample of blood from a user in response to a trigger signal generated based on a user input;
   a determining unit configured to
   (a) use information provided by one or more sensors to determine a level of intensity of physical activity in each of plural consecutive time periods and to record a value for the determined level of intensity along with an indication of an associated time period in the storage unit,
   (b) use information provided by the one or more sensors to calculate a measure of physical activity of the user, and
   (c) calculate a medicament dose using at least the measured glucose level and the measure of physical activity of the user, and a time elapsed between an instance of physical activity and a current time and to afford a higher weight
      (i) to an instance of physical activity occurring more recently with respect to the current time, and
      (ii) to an instance of physical activity having a higher level of intensity such that the higher level of intensity results in a disproportionately greater increase in the weight afforded to the medicament dose than a respective recorded value of the determined level of intensity; and
   a display unit configured to indicate the calculated medicament dose to the user.

2. A device as claimed in claim 1, wherein the determining unit is further configured to use at least one measure of physical activity intensity to calculate the medicament dose.

3. A device as claimed in claim 1, wherein the determining unit is further configured to use a duration of physical activity to calculate the medicament dose.

4. A device as claimed in claim 3, wherein the determining unit is configured to integrate the physical activity intensity with respect to time and to use the result of the integration to calculate the medicament dose.

5. A device as claimed in claim 1 wherein the one or more sensors include a pedometer and the measure of physical activity is a number of steps taken by the user within a predetermined period.

6. A device as claimed in claim 5, wherein the pedometer is integrated with the device.

7. A device as claimed in claim 1, wherein the one or more sensors include an accelerometer integrated with the device.

8. A device as claimed in claim 1, wherein the device includes a communications receiver configured to receive information from external one or more sensors.

9. A device as claimed in claim 8, wherein the device is configured to verify that information received using the communications receiver relates to a user registered with the device and to disregard information other than verified information when calculating the medicament dose.

10. A device as claimed in claim 8, wherein the device is configured to receive information relating to heart rate and/or blood pressure of a user and to calculate the measure of physical activity by processing the heart rate and/or blood pressure information.

11. A device as claimed in claim 8, wherein the device is configured to receive information relating to a number of steps taken by a user from an external pedometer and to calculate the measure of physical activity by processing the steps information.

12. A device as claimed in claim 8, wherein the device is configured to receive information relating to work done by the user or power exerted by the user from an external ergometer and to calculate the measure of physical activity by processing the work done or power information.

13. A method of operating a device, the method comprising:
   obtaining a measure of a glucose level of a sample of blood from a user in response to a trigger signal generated based on a user input;
   using information provided by one or more sensors to determine a level of intensity of physical activity in each of plural consecutive time periods and to record the determined intensity information along with an indication of the associated time period in a storage unit;
   using information provided by the one or more sensors to calculate a measure of physical activity of the user;
   calculating a medicament dose using at least the measured parameter, the measure of physical activity of the user and a time elapsed between an instance of physical activity and a current time and affording a higher weight
      (i) to an instance of physical activity occurring more recently with respect to the current time, and
      (ii) to an instance of physical activity having a higher level of intensity such that the higher level of intensity results in a disproportionately greater increase in the weight afforded to the medicament dose than a respective recorded value of the determined level of intensity; and
   indicating the calculated medicament dose to the user.

* * * * *